(12) United States Patent
Ilan (10) Patent No.: US 11,881,296 B2
(45) Date of Patent: Jan. 23, 2024

(54) IDENTIFYING AND QUANTIFYING INDIVIDUALIZED VARIABILITY-PATTERNS AND IMPLEMENTING THEM FOR IMPROVED EFFICACY OF SYSTEMS

(71) Applicant: OBERON SCIENCES ILAN LTD., Kfar Tavor (IL)

(72) Inventor: Yaron Ilan, Kfar Tavor (IL)

(73) Assignee: OBERON SCIENCES ILAN LTD., Klar Tavor (IL)

( * ) Notice: Subject to any disclaimer, the term of this patent is extended or adjusted under 35 U.S.C. 154(b) by 860 days.

(21) Appl. No.: 16/782,248

(22) Filed: Feb. 5, 2020

(65) Prior Publication Data
US 2020/0251201 A1    Aug. 6, 2020

Related U.S. Application Data

(60) Provisional application No. 62/801,770, filed on Feb. 6, 2019.

(51) Int. Cl.
*G16H 20/17* (2018.01)
*A61M 1/14* (2006.01)
(Continued)

(52) U.S. Cl.
CPC .............. *G16H 20/17* (2018.01); *A61M 1/14* (2013.01); *A61M 5/1723* (2013.01);
(Continued)

(58) Field of Classification Search
CPC ......... G16H 20/17; G16H 70/20; A61M 1/14; A61M 5/1723; A61M 16/026; A61N 1/365; G06F 7/582; G06F 7/588; G06N 20/00
See application file for complete search history.

(56) References Cited

U.S. PATENT DOCUMENTS

2011/0264378 A1*  10/2011  Breton ................. A61B 5/0002
                                                    702/19
2014/0136583 A1*  5/2014   Hyde ...................... G06F 7/588
                                                    708/250
(Continued)

OTHER PUBLICATIONS

Avolio, A "Heart rate variability and stroke: strange attractors with loss of complexity", Journal of Hypertension, vol. 31(8): 1529-1531, (2013).
(Continued)

*Primary Examiner* — Robert A Sorey
*Assistant Examiner* — Kristine K Rapillo
(74) *Attorney, Agent, or Firm* — The Roy Gross Law Firm, LLC; Roy Gross (57) ABSTRACT

The disclosure provides methods for improving the function of systems regimens, devices by identifying, quantifying, and implementing at least one inherent variability pattern which is based on patterns learned from a specific subject or from other subjects including subject's variability patterns, such as, DNA, genes, nucleic acids, RNA, proteins, cells, organs, biological pathway(s), or whole body variability. There are provided herein devices, systems, and methods for real time or delayed altering of the parameters of system's regimens, for improving biological systems functions. Any system used by humans, or affect human function, wherein the parameters are updated using inherent variabilities signatures with and without other individualized patterns from a subject or from other subjects, can increase the accuracy and efficacy of the system for achieving the desired goal. Output parameters are continuously, semi continuously, or conditionally being updated based on measurements and inputs provided to a compute circuitry configured to facilitate closed loop machine learning capabilities.

15 Claims, 1 Drawing Sheet

(51) Int. Cl.
  A61M 5/172    (2006.01)
  A61M 16/00    (2006.01)
  G16H 70/20    (2018.01)
  G06N 20/00    (2019.01)
  G06F 7/58     (2006.01)
  A61N 1/365    (2006.01)
(52) U.S. Cl.
  CPC .......... *A61M 16/026* (2017.08); *A61N 1/365* (2013.01); *G06F 7/582* (2013.01); *G06F 7/588* (2013.01); *G06N 20/00* (2019.01); *G16H 70/20* (2018.01)

(56) References Cited

U.S. PATENT DOCUMENTS

2017/0157410 A1* 6/2017 Moffitt ................ G16H 70/20
2017/0220751 A1* 8/2017 Davis .................... G06N 5/048

OTHER PUBLICATIONS

Bandiera, et al., "Phenotypic Variability in Synthetic Biology Applications: Dealing with Noise in Microbial Gene Expression", Frontiers in Microbiology, vol. 7: 479 (2016).
Berlim, et al., "Current trends in the assessment and somatic treatment of resistant/refractory major depression: an overview", Annals of Medicine, vol. 40(2): 149-159 (2008).
Contin, et al., "Intrapatient variation in antiepileptic drug plasma concentration after generic substitution vs stable brand-name drug regimens", Epilepsy Research, vol. 122: 79-83 (2016).
Costa, et al., "Dynamical glucometry: Use of multiscale entropy analysis in diabetes", Chaos; An Interdisciplinary Journal of Nonlinear Science, vol. 24(3): 033139 (2014).
Dai, et al., "The Regulatory Mechanisms and Therapeutic Potential of MicroRNAs: From Chronic Pain to Morphine Tolerance", Frontiers in Molecular Neuroscience, vol. 11: 80 (2018).
Elgart, et al., "Determinants of drug-target interactions at the single cell level", PLOS Computational Biology, vol. 14 (12): e1006601 (2018).
Emara, et al., "Single-Cell Metabolomics", Advances in Experimental Medicine and Biology, vol. 965: 323-343 (2017).
Goldberger, A. L. "Non-linear dynamics for clinicians: chaos theory, fractals, and complexity at the bedside", The Lancet, vol. 347(9011): 1312-1314 (1996).
Gueta, et al., "High tacrolimus trough level variability is associated with rejections after heart transplant", American Journal of Transplantation, vol. 18(10): 2571-2578 (2018).
Jardim, et al., "A 2018 overview of diuretic resistance in heart failure", Portuguese Journal of Cardiology, vol. 37(11): 935-945 (2018).
Johnston, et al., "The burden of treatment-resistant depression: A systematic review of the economic and quality of life literature", Journal of Affective Disorders, vol. 242: 195-210 (2019).
Kalden, et al., "Immunogenicity and loss of response to TNF inhibitors: implications for rheumatoid arthritis treatment", Nature Reviews Rheumatology, vol. 13(12): 707-718 (2017).
Kïnig, et al., "Can Gait Signatures Provide Quantitative Measures for Aiding Clinical Decision-Making? A Systematic Meta-Analysis of Gait Variability Behavior in Patients with Parkinson's Disease", Frontiers in Human Neuroscience, vol. 10: 319 (2016).
Lafzi, et al., "Tutorial: guidelines for the experimental design of single-cell RNA sequencing studies", Nature Protocols, vol. 13(12): 2742-2757 (2018).
Mariani, et al., "Analysis of the Sleep EEG in the Complexity Domain", Conf. Proc. IEEE Eng Med Biol Soc 2016: 6429-6432 (2016).
Moon, et al., "Gait variability in people with neurological disorders: A systematic review and meta-analysis", Human Movement Science, vol. 47:197-208 (2016).
Nayyar, et al., "Effect of Loss of Heart Rate Variability on T-Wave Heterogeneity and QT Variability in Heart Failure Patients: Implications in Ventricular Arrhythmogenesis", Cardiovascular Engineering and Technology, vol. 8(2): 219-228 (2017).
Robinette, B :Strategies to overcome diuretic resistance in congestive HF, Cardiology Today, Feb. 2015.
Sacks, et al., "The Economic Burden of Insulin Resistance, Obesity, and Cardiovascular Disease in Medicare Beneficiaries 65 Years of Age and Older", Circulation 136: A15099 (2018).
Shah, et al., "A perspective on diuretic resistance in chronic congestive heart failure", Therapeutic Advances in Cardiovascular Disease, vol. 11(10): 271-278 (2017).
Singh, et al., "Heart Rate Variability: An Old Metric with New Meaning in the Era of using mHealth Technologies for Health and Exercise Training Guidance. Part One: Physiology and Methods", Arrhythmia & Electrophysiology Review vol. 9(3): 193-198 (2018).
Skånland, S.S. "Phospho Flow Cytometry with Fluorescent Cell Barcoding for Single Cell Signaling Analysis and Biomarker Discovery", Journal of Visualized Experiments, (140) (2018).
Su, et al., Single cell Proteomics in Biomedicine: High-dimensional Data Acquisition, Visualization and Analysis, Proteomics, vol. 17 (3-4) (2017).
Tang, et al., "Drug-Resistant Epilepsy: Multiple Hypotheses, Few Answers", Frontiers in Neurology, vol. 8: 301 (2017).
Ter Maaten, et al., "Renal tubular resistance is the primary driver for loop diuretic resistance in acute heart failure", European Journal of Heart Failure, vol. 19(8): 1014-1022 (2017).
Toni, et al., "Combined Model of Intrinsic and Extrinsic Variability for Computational Network Design with Application to Synthetic Biology", PLOS Computational Biology, vol. 9(3): e1002960, (2013).
Xia, et al., "Cell-to-cell variability in cell death: can systems biology help us make sense of it all?" Cell Death and Disease, vol. 5: e1261 (2014).
Yach, et al., "The Global Burden of Chronic Diseases: Overcoming Impediments to Prevention and Control", The Journal of the American Medical Association, vol. 291(21): 2616-2622) (2004).

* cited by examiner

IDENTIFYING AND QUANTIFYING INDIVIDUALIZED VARIABILITY-PATTERNS AND IMPLEMENTING THEM FOR IMPROVED EFFICACY OF SYSTEMS

CROSS REFERENCE TO RELATED APPLICATIONS

This application is a non-provisional which claims the benefit of and priority to U.S. Provisional Application No. 62/801,770 filed on Feb. 6, 2019. The contents of the above application is incorporated by reference in its entirety.

TECHNICAL FIELD

The disclosure generally relates to the field of improving function of systems by identifying and quantifying individualized variability patterns and implementing them into these systems.

BACKGROUND

Chronic disease is defined by the World Health Organization (WHO) as being of long duration, generally slow in progression and not passed from person to person. The prevalence of chronic condition multi-morbidity increases with age. About 40% of people aged over 44 years have chronic disease multi-morbidity, increasing to around 50% for 65-74 years old, and 70% above the age of 85 years. In 2014, 60 percent of Americans had at least one chronic condition, and 42 percent had multiple chronic conditions. Chronic diseases are the largest cause of death in the world. Ageing of the world's population is leading to a significant increase in the numbers of individuals with chronic diseases.

Drug tolerance is associated with resistance to therapy and partial or complete loss of effects of medications and has a major impact on the outcome of major chronic diseases. Some common examples are: insulin resistance in patients with diabetes; loss of effect to anti-epileptics; diuretic resistance in congestive heart failure; loss of responsiveness to immunomodulators in patients with inflammatory bowel disease and arthritis; tolerance to anti-depressants; and tolerance to painkillers. Resistance is associated with poor prognosis. Insulin resistance is associated with high rates of cardiovascular disease, hospitalization, and health care spending. Increasing dosages in an attempt to overcome resistance, may further increase the resistance leading to clinical deterioration due to loss of an effect.

Patients respond differently to similar treatments. Most drugs and therapies are developed for the "average patient," a method which does not fit many of the individual subjects. The inter-individual variation in drug response is driven in part by differences in multiple parameters. Using averages in medicine is insufficient for developing personalized medicine. However, for most diseases there are not valid enough methods of knowing which treatment may work best for an individual subject. Attempts of using genotype, phenotype, and other "personalized" measures, are only partially successful in overcoming the problem of improving the response to chronic therapies in an individualized way.

Biological systems are inherently variable, with their dynamics affected by both intrinsic and extrinsic sources. The inherent variability can be detected at the level of the genes, with genetic heterogeneity among adjacent cells, RNA, proteins, cellular function, including metabolic heterogeneity among adjacent cells, function of cell apparatuses, organ function, and whole-body heterogeneity. These systems are often only partially characterized, with large uncertainties about specific sources of the intrinsic and extrinsic variabilities and biochemical or other body properties.

Inherent intra & inter-patient's variabilities patterns were described for many biological systems. Examples are heart rate variability, breathing variability, gate variability, and others. Loss or change of theses normal physiologic variabilities is associated with poor prognosis.

Stochasticity at the cell level is associated with collisions among low copy-number molecules within the crowded cellular compartment. Single cell variability in gene expression is a result of both intrinsic and extrinsic stochasticity. Intrinsic stochasticity arises from the random occurrence of events inherent to the gene expression process including synthesis of mRNA and protein molecules. Extrinsic fluctuations reflect the state of the biological system and its interaction with the intra and extracellular environments.

For cell death, not all cells die at the same time, or at the same treatment dose. This cell-to-cell variability is a result of unpredictability of apoptosis signaling networks, intracellular, and extracellular parameters. Intra and inter cell variabilities also occur for cell phenotypes manifested by marked heterogeneity in the expression of cell epitopes, cell singling pathways, and cytokine secretion.

High degree of both intra and inter patient variability was described for the pharmacokinetics and the response to drugs. This variability is associated with reduction of efficacy and even with loss of effect to drugs. High intra-patient tacrolimus variability was associated with graft rejection. Intrapatient variability in anti-epileptic plasma levels in patients stabilized with the same product over time was described with differences of tens of percentages in serum levels among patients. At the cellular level, the cell is crowded with a non-uniform distribution of macromolecules that interact with a drug specifically and nonspecifically. This leads to a high degree of variability between adjacent individual cells in the response to drugs. The marked inherent intra and inter-patient's variabilities impact drug metabolism and response to therapies.

Thus, "regular" drug dosing regimens are not compatible with the inherent intra and inter patient variability, and further increase drug-resistance. To successfully design biomedical therapies, it is required to consider the uncertainty and effects of variability.

Human driving is affected by variable responses to triggers which affect both the safety and pleasure of the drive. These variable responses are both intra and inter individuals. Autonomous cars may be associated with unpleasant monotonic drive which is not suitable to the passengers, and may also jeopardizes their safety.

The use of randomness in security is employed by using algorithms which determine type, number, and schedules of patrols. Variability and randomness are used in cyber security algorithms and for encryption and cryptography. These random measures are not individualized and have caveats which reduce their level of protection.

Many devices used by humans involve mechanical or electronic engines, or are computer-controlled, are designed to function in a constant regular way which is not personalized.

There is therefore a need to individualized the functions and activities of operation regimens and devices, in a way which would improves the efficacy of systems, which are related, directly or indirectly, to humans.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there are provided methods to identify intra and inter subject variability patterns from the cellular to whole organ, and whole body levels, identify methods to quantify them, combine them with other patterns of variability and/or with other personalized patterns, from the same subject, and from other subjects, and incorporate them into methods and algorithms which are aimed at improving the function of systems.

The embodiments show that a personalized-based inherent variability patterns which can be learned from an individual or a group of individuals can be quantified and implemented for improved functions of systems used by or for humans.

In accordance with some embodiments the identified variability patterns are at the level of genes, gene networks, RNA, proteins, cell apparatus, organs, proteome, metabolome, lipidome, transcriptome, whole body, or any type of network patterns. They comprise both intra and inter subject-type of variabilities patterns. These patterns may be constant or change over time.

In accordance with some embodiments, there are provided herein methods and/or algorithm-based methods, which are based on subject specific-variability patterns, and used for improvement of the efficacy of drugs, devices, cars, function of autonomous cars, cyber security, cryptography, training, electronic devices, mechanical devices, search engines, or systems used by humans, or for humans, and/or any combination thereof.

In accordance with some embodiments, there are provides herein subject-tailored, variability patterns from the levels of genes, gene networks, RNA, proteins, cells, organs, transcriptome, metabolome, proteome, lipidome, whole body, or any type of network, continuously or semi-continuously developing, closed-loop method(s) and/or device(s)/system(s) implementing these variability signatures for improving the function of systems.

In accordance with some embodiments, there are provides herein method(s) and/or device(s)/system(s) implying the method(s), for improving efficacy of systems in the body or outside the body including drugs, medical devices, pumps, cars, security programs, cryptography, household devices, electronic devices, mechanical devices, search engines, and other systems which are used by, or for, humans, in a direct or an indirect way. A subject-tailoring is performed by implementing the subject's own variability patterns, with or without other personal patterns, and may include in addition patterns learned from other subjects, into the function of these systems while adjusting them to the pre-determined goals.

According to some embodiments, the machine learning capabilities include closed-loop deep learning. According to some embodiments, the machine learning capabilities are configured to be operated on a set of features by receiving values thereof. According to some embodiments they can quantify one or more of the personalized variability parameters to generate a number(s)/factor(s), with or without combining them with non-variable personalized patterns, and/or combining them with patterns from other subjects, and implement them into a method or an operating method and/or an algorithm for improving the function of a system. Some of these parameters may be subject's specific, and some may be learned from other populations, or may also be random parameters.

According to some embodiments, the method may be used for improving organ function in healthy or sick subjects who wish to improve muscle, heart, lung, skin, brain on any other tissue/organ/organs performance, and/or for improving training capabilities of any tissue/organ/organs, improving education, or teaching, and/or for treatment of obesity, infectious, metabolic, endocrinology, malignant, immune-mediated, inflammatory condition, inborn error of metabolism, pain, microbiome-related disorders, neurological disease, fibrosis in an organ, desynchronosis or circadian dysrhythmia.

According to some embodiments, the method may be used for improving driving capabilities, safety, and pleasure of driving, of a human driver, or for improving the user experience and safety of passengers using autonomous cars.

According to some embodiments, the method may be used for improving the function and degree of protection of cyber security algorithms, encryption and cryptography, in a personalized way.

According to some embodiments, the method may be used for improving the function and experience of using any device or system which are used by humans, or for humans, by implementing subject's-tailored parameters into the system. This include coffee makers, soda machines, electrical bicycles, music devices, smart phones, personal computers, search engines, and any type of mechanical or electronic device, or device or methods which are used by or for humans, and are associated in a direct on an indirect way with humans.

According to some embodiments, the processor is further configured to identify and select methods for to quantify, intra and inter subjects-tailored inherent variability patterns from studying subject's genes, gene networks, RNA, proteins, cellular apparatus, cell function, proteome, metabolome, lipidome, microbiome, organs, or whole body, or any type of network, continuously or semi continuously, ongoing developed variability or variabilities-patterns-based algorithms configured for improving function and/or performance thereof of any system which is used by or for humans, and is associated in a direct on an indirect way with humans.

According to some embodiments, there is provided herein a method for improving function of one or more biological system of a subject in an individualized way, and/or for overcoming partial or complete loss of effect, non-responsiveness, and/or partial or complete resistance of one or more biological systems to a treatment regimen or to any type of a trigger whether internal or external to the system, by identifying, quantifying, and/or implementing at least one inherent variability pattern, which is based on patterns learned from the subject and/or from other subjects, and or the environment, the method comprising: identifying intra subject and/or inter subjects variability patterns, and combining them with non-variable individualized patterns and/or networks, for generating individualized-regimen-based system operating methods or algorithms; identifying one or more methods to quantify one or more variability patterns, nonlinear networks and chaotic parameters, and combining them with variability and/or non-variability individualized patterns from one or more subjects; identifying methods to incorporate one or more variability and/or non-variability patterns into treatment regimens or operating algorithms; receiving a plurality of physiological and/or pathological inherent patterns of variability with and without additional parameters related/unrelated to a target system, and/or related/unrelated to the subject; applying a closed-loop machine learning algorithm to a plurality of target system parameters; determining subject-specific output parameters relating to at least one target system function; and utilizing the subject-specific output parameters to improve the at least one target system function by using the machine learning algorithm by applying a subject-tailored continuously or semi continuously inherent variability patterns, thereby facilitating continual improvement of the target system; and incorporating individualized parameters based on variability-patterns as well as other personalized signatures, into irregularity generating-algorithms for improving the at least one target system function.

According to some embodiments, the at least one inherent variability pattern may include: variability patterns at the level of DNA, RNA, proteins, cellular functions, cell signaling products, cell apparatuses, body organs, biological pathway(s), proteome, metabolome, lipidome, microbiome, organs, whole body and/or any type of network-based variability, including internal and external triggers, including environment-associated conditions.

According to some embodiments, the method may further be utilized for improving function and/or performance thereof and for individualizing treatment regimens and/or devices and for improving their efficacy for reaching goals determined by the subject, the system, or by other subjects, optionally additionally using updated at least one of the subject-specific output parameters.

According to some embodiments, the machine learning algorithm takes into account personal data including any type of individualized-inherent variability patterns and wherein at least one of the physiological and/or pathological parameters is obtained from a sensor.

According to some embodiments, the method may further include providing to the subject, to a device, or to the target system a recommended regimen or changes thereto.

According to some embodiments, the of the providing of the recommended regimen or changes thereto is in real time.

According to some embodiments, the machine learning capabilities may include closed-loop deep learning capabilities and are configured to operate on a set of features by receiving values thereof.

According to some embodiments, the method may be used for improving tissue, organ and/or body system function in healthy or sick subjects, wherein the tissue, organ and/or body system comprises: muscle, heart, lung, skin, brain, liver, pancreas, bladder, uterus, kidney, cardio vascular system, lymphatic system, immune system, hormonal system, genital system, nerve system, skeletal system or any combination thereof.

According to some embodiments, the method may be used for improving training, learning and/or teaching capabilities.

According to some embodiments, the method may be used for treatment of obesity, infectious, metabolic, endocrinology, malignant, immune-mediated, inflammatory condition, inborn error of metabolism, pain, microbiome-related disorders, neurological disease, fibrosis in an organ, desynchronosis, circadian dysrhythmia or any combination thereof.

According to some embodiments, the method may be used for improving drug treatment regimens, redesigning of structure of drugs, for overcoming drug resistance, for improving a clinical effect of a medical device.

According to some embodiments, the medical device may include a pacemaker, ventilator, dialysis machine, pump for delivering drugs.

According to some embodiments, the irregularity generating algorithms may include random or pseudo random number generating algorithms.

According to some embodiments, there is provided herein a method for improving function of a computerized system having learning capabilities, the method comprising: obtaining an intra computerized system and/or inter computerized systems variability patterns, and combining them with non-variable patterns and/or networks, for generating system-tailored operating methods or algorithms; identifying one or more methods to quantify one or more variability patterns, nonlinear networks and chaotic parameters, and combining them with variability and/or non-variability patterns from one or more systems; identifying methods to incorporate one or more variability and/or non-variability patterns into the system-tailored operating methods or algorithms; receiving a plurality of hardware and/or software inherent patterns of variability with and without additional parameters related/unrelated to the computerized system; applying a closed-loop machine learning algorithm to a plurality of parameters characterizing one or more functions of the computerized system; determining system-tailored output parameters relating to the one or more functions; and utilizing the system-tailored output parameters to improve the one or more functions by using the machine learning algorithm by applying a system-tailored continuously or semi continuously inherent variability patterns, thereby facilitating continual improvement of the computerized system; and incorporating system-tailored parameters based on variability-patterns as well as other system specific signatures, into irregularity generating-algorithms for improving the one or more functions.

According to some embodiments, the computerized system may include driver-controlled cars or an autonomous car.

According to some embodiments, the computerized system comprises a mechanical and electronic device.

According to some embodiments, the computerized system comprises a smartphone, a smartwatch, a tablet or any combination thereof.

According to some embodiments, the method may be used for improving output of a search engine, for improving level of security of algorithms used in cyber security or cryptography, for improving cloud-based services and/or for robotic system.

According to some embodiments, the irregularity generating algorithms may include random or pseudo random number generating algorithms.

According to some embodiments, the computerized system may include an artificial neural network.

According to some embodiments, there is provided herein a computerized system configured to implement any one or any combination of the methods disclosed herein.

According to some embodiments, there is provided herein a computer readable storage medium comprising instructions which cause one or more processors to perform any one or any combination of the methods disclosed herein.

BRIEF DESCRIPTION OF THE DRAWINGS

Examples illustrative of embodiments are described below with reference to FIGURES attached hereto. In the FIGURES, identical structures, elements or parts that appear in more than one FIGURE are generally labeled with the same numeral in all the FIGURES in which they appear. Alternatively, elements or parts that appear in more than one FIGURE may be labeled with different numerals in the different FIGURES in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there are provided herein algorithms, methods, devices, and systems for improving organ function or system function, or a regimen, or quality of security algorithms, or cars, or performance of device or system which is used by or for humans, by implementing patterns of intra and inter subject variabilities, with and without combining them with non-variable individualized patterns, with or without adding patterns learned from other subjects, that are identified from the human body as part of the inherent variability/variabilities of DNA, RNA, gene networks, proteins, cells, cellular apparatuses, organs, proteome, lipidome, metabolome, microbiome, whole body, or any other body network or signature.

According to some embodiments, there are provided herein devices, systems and methods for using identified patterns of variability for improving functions of systems.

According to some embodiments, there are provided herein devices, systems and methods for quantifying these parameters, and generating number(s)/factor(s) which can be implemented into a functional regimen/an operating algorithm, for improving the function of a system.

According to some embodiments, out of these variability patterns, an individualized pattern-based number(s)/factor(s) are generated, and implemented into the operating method of system. For example, the ratio between two heart beat variabilities from two consecutive beats; mean of ratios between consecutive variabilities in heart rate; ratios between two or more breathing variabilities; any type of sample entropy algorithm; use of a complexity index; multiscale entropy measurements; methods used to quantify nonlinear or chaotic systems; using the ratio between differences between cells in gene expression, proteomics or metabolomics at a level of single cells or multiple cells; or any combination of these; are implemented into operating systems aiming at improving the function of systems, or into algorithms which control the function of systems in the human body, or of any device or method being used by humans, or for humans.

According to some embodiments any output of function of a body organ, car function, learning ability, exercise, nutritional regimen, device which administer drugs such as pumps, pacemakers, ventilators, drug regimens including alternating between different drugs which can target the same disease for the same patient, design of drugs' structures, dialysis machines, function of home devices, machine which prepare a personalized-coffee in a dynamic way, a smart phone which is being dynamically-personalized by altering its volume, lightening of screen, or any other parameters which can be changed, function of devices used by humans for any purpose whether personal or non-personal, algorithms designed for improving security, can be improved by implementing parameters which are based partially or solely on inherent types of variability patterns from the user or other users, and can be combined with additional parameters whether relevant or irrelevant to the function of the system, including individualized and non-individualized parameters which are not variable, any type of body networks, combining them with parameters from other subjects or other systems, for achieving the desired goal or for improving the overall function of the system in a dynamic-personalized way.

According to some embodiments, the parameters are determined and updated using a machine learning system, which provides parameter values based on feature values received from and/or related to the user and to their performances. According to some embodiments, the machine learning system may be a deep learning system, in which the learning on some features is guided or supervised learning, while learning on other features is unguided or unsupervised learning. According to some embodiments, the number of layers/levels of the deep machine learning depends on the number of features.

According to some embodiments, the user updates the machine with progress towards the target goal, which set by the subject, or defined for subject, for improving function of a system towards a required level, for an overall improvement of organ or system performance. The learning machine provides updated functional regimens-relevant parameters and regimens, and/or stimulation or other device-related parameters based on data learned from the target organ or target system function, and/or subject performance, and/or disease, and/or medications, and/or a subject or subgroup of subjects, and/or type of exercise/training/teaching/learning/education/nutritional regimen, and/or security protocol regimens and car driving including autonomous cars, or cyber security regimens, cryptography regimens, any type of device used by humans, including coffee makers, soda machines, electrical bicycles, music devices, smart phones, and personal computers, search engines, cloud-based voice services, and robots which work for or with humans.

According to some embodiments, the user updates the machine with related or non-related inherent variability parameters with or without additional biomarkers or parameters, or combinations of regimens and/or user and/or other users, that may be given to other users with similar feature values such as performance, scores related to the target function, conditions and so on, as well as data specific to the user, for example progress towards improving the function and pleasure of using a device, and the like.

According to some embodiments, user inputs may include all types of physiological or pathological parameters, personal and environmental parameters which are relevant directly or indirectly to target system regimens or procedures. These parameters may be of relevance to a subject, or to a specific regimen, or to a specific organ, or system, and not necessarily to all subjects. The input parameters may involve one or more patterns of inherent variability from different levels in the subject body and/or from other subjects. These parameters may be used on their own, or may be combined with other parameters.

According to some embodiments, any type of quantification method or methods can be used for generating number(s)/factor(s), or any other method for quantifying the pattern(s) of variability, and combining them with non-variable parameters, and with any other type of parameters, signatures, or networks, and implement them into the function of a system, or into an algorithm to be used for improvement of the function of systems. These include any type of entropy type of algorithms, indexes used for analyzing irregularity, methods for quantifying networks, methods for quantifying chaotic and non-linear systems, and alike.

According to some embodiments, the user may update the machine, or the machine may receive inputs from the user and/or from other users, to inform the algorithm in a way that enable to redirect or further define the function of the algorithm, or the device, or the treatment regimen, or the function of an engine, or the performance of a system, to the user, following a closed-loop system.

The data received in real time or not, is continuously analyzed based on one subject's pattern of variability, and/or subgroups of subjects, system function parameters, and biomarkers which are directly and indirectly associated with the system, the subject, subject performance, system performance, and data from other subjects.

As used herein, the terms "learning machine", "update module" and "update system" are interchangeably used, and refer to an integrated or communicatively linked component of the system, which is configured to receive input data in form of user data, or any type of variability pattern, define a method to quantify the input, and has an option to combine it with data from the subject or other subjects which is not necessarily based on variability patterns. These patterns or parameters are directly or indirectly associated with the function of the system, and can include features which measure directly or indirectly relevant human indications. The learning machine can implement the data from these patterns into functional parameters of the system, or into an algorithm which impacts the function of the target system to reach an endpoint which is predefined by the user or by the system, or by other subjects.

According to some embodiments, the input data on the user along with the input received from other users on a continuous or semi continuous basis is processed by the controller, which is based on a closed-loop system that continuously evaluates the distance of the tested parameter from the level to be achieved or the direction and/or rate of changes in the physiological or pathological measurement/parameter, generates an improved algorithm being transformed into new output.

The output may be in a form of an alert delivered to the subject or to a device, a car, an engine, a system associated with humans, an algorithm-based security, via a cell phone-based application, or by any other method, which may alter the function of the target system, or the function regimen of the target system for improving their function.

Figure 1:
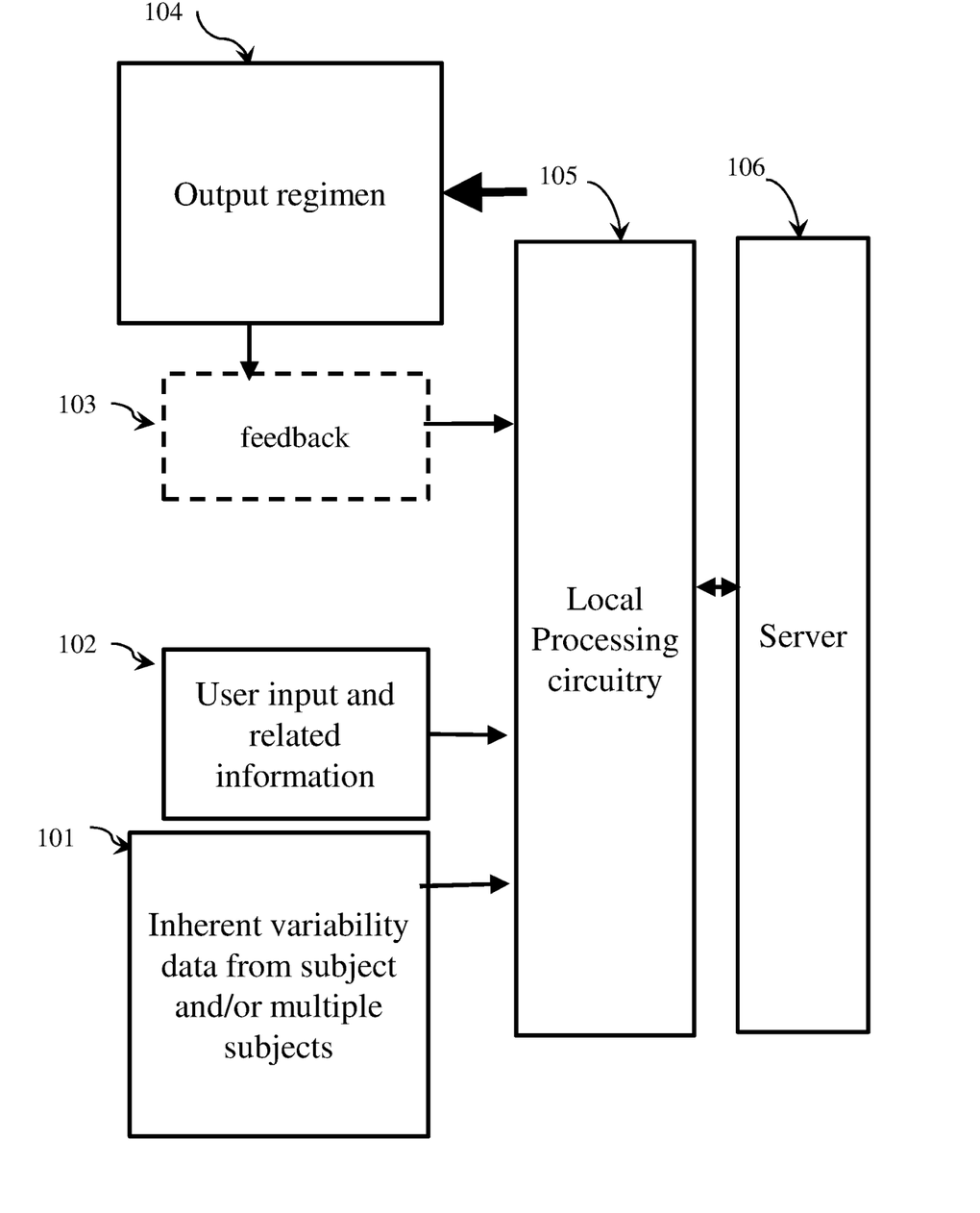
FIG. 1 schematically illustrates a functional block diagram of a system, which accumulates subject-related inherent variability patterns from tests done on subject and/or other subjects DNA, gene networks, RNA, proteins, cells, cell apparatus, organs, proteome, lipidome, metabolome, microbiome, whole body, or any type of network or signature. These inherent variability patterns may be also combined with non-variability individualized patterns, and with patterns from other subjects, are quantified using various methods, processed and incorporated into an operation regimens and/or algorithms which improve the function of a device, a drug therapeutic regimen, drug structure, cryptography algorithm, car function-related algorithm, cyber security algorithm, search engine, and any device or system which are used by or for humans, and are associated in a direct on an indirect way with humans.

Reference is now made to FIG. 1. According to some embodiments, system 100 includes a challenged-functional regimen alert output device and/or maneuver/stimulator 104, which is configured to provide function regimen alert output to a target system (any organ in the body (such as brain, heart, kidney, leg, hand and the like and any tissue, such as muscles, connective tissue, epithelial cells or nerves), a car, an engine, a medical device, a household device, a cyber-security protocol, any type of security protocol, a search engine, and any system which is directly or indirectly used for or by humans), to achieve a desired goal as determined by the user, or by others, or a physiological effect for improving of system function, optionally one feedback mechanism 103 associated with function output and/or maneuver/stimulator 104, configured to provide measurements of functional indicators relevant to target system function, or any other system related or non-related parameter, or alternatively, technical information related to the system. These parameters may be related, or indirectly related, to the target system, which the method or the algorithm are aimed at improving its performance.

According to some embodiments, system 100 further includes additional external sensors, which can receive or identify inherent variability patterns 101 to be incorporated into the output following being processed by a processing device 105, and user inputs and/or other related information 102, which also uses one or more methods for quantifying these patterns. These include methods for quantifying networks, quantification of chaotic systems, and of non-linear systems. For example, variability patterns of pulse, rate of breathing, oxygen saturation, pulmonary artery pressure, which provide data on the heart function or on overall body function, can be implemented with the other inherent variability patterns such as gene networks, or protein-based variability patterns, of the subject, for generating number(s)/factor(s), which are used for improving the function of a pacemaker or a ventilator, or a dialysis machine of the subject. The information from feedback mechanism 103 is provided to a local processing circuitry, which is configured to control the operation of 104 based on inputs that include measurements of external or internal sensors, inherent variability patterns 101 and user inputs and/or other related information 102, and optional feedback mechanism 103.

According to some embodiments, a user may be instructed or advised to measure their organ function and/or regimen and/or disease-associated biomarker periodically, or provide an inherent variability patterns periodically, or continuously, aiming to achieving the goal, at certain times or after/at/before certain events. According to some embodiments, processing circuitry 105 may be in communication with a remote server 106 for tapping into the computing performance thereof, and/or data of previous/other users. According to some embodiments, remote server 106 may be a cloud computer. According to some embodiments, processing circuitry is designed for a continuous or semi continuous closed loop data input and output, wherein algorithm output and/or device-generated maneuver or stimulation parameters are adjusted based on the input information and data.

According to some embodiments, the output algorithm may be introduced by a new function regimen and/or by a device-generated maneuver. It may be introduced to provide an alert for a preferred function regimen to achieved the desired goal for that system.

According to some embodiments, the method/system disclosed herein may be used for improvement of function of a system, a machine, a device, a search engine, security algorithms, which are used by humans, or for humans, in a direct or an indirect way, for continuous improving and reaching a better goal in their function. The target is defined by the subject, or by the system itself in a subject's-tailored way, or by other subjects.

According to some embodiments, a clinically meaningful-endpoint, or subject's determined goal, may be pre-determined for the algorithm, and several individualized-variability signatures, using one or more methods for quantifying them, and implementing them into a method of function or into an algorithm are used based on the patient's response.

According to some embodiments, the algorithm can incorporate data generated from other subjects and can identify the preferred variability patterns and/or other patterns based on which to determine a subject's-tailored irregularity in the function of a system.

According to some embodiments, the algorithm can also identify other methods for quantifying the patterns of variability such that a better end response is noted. The number (s)/factor(s) generated from one or more of the inherent individualized patterns are incorporated into the operating system which for example determine dosage and time interval ranges for drug administration, drug structure, or function of any system. These numbers are used for generating a personalized-type of irregularity of the operating system, or any type of alteration of the operating system by which to improve its function. Irregularity is a random perturbation with the power of randomness which is exploited to enhance systems functions.

According to some embodiments, an alert is delivered via a cloud based alert system, for example, in real time, such that the alert is connected to any type of partial/complete loss of an effect, of regimens and/or device treatment or maneuver.

EXAMPLES

Example 1: Identifying and Quantifying Intracellular Patterns of Variability

Single cell heterogeneity is shown for many cellular expressions. These include marked variability of single cell response to therapy, such that adjacent cells within the same tumor respond differently to chemotherapy; there is marked heterogeneity in the single cells metabolic function for cells from the same subject and from the same organ; cellular heterogeneity is shown in the genetic level for adjacent cells; immune phenotyping, and immune cells movements show marked heterogeneity for expression of epitopes, and for their functional parameters, such as the secretion of cytokines. Inherent variability patterns from the levels of genes, RNA, proteins, cells, cell apparatuses, body organs, body tissues, transcriptome, proteome, metabolome, lipidome, microbiome, and/or whole body, are used to identify biological pathways to be targeted by therapies. They enable optimizing artificial gene circuitry for industrial applications and synthetic biology. Intracellular, and intra organ type of variabilities impact the selection of network(s) to be targeted by therapies. Identifying patterns of variabilities in cell death are used for determining the response to drug, selecting right dosing scheduling of drugs aimed at preventing cell death, and structuring new molecules with better effects. It can assist in strategies to manipulate death of cancer cells.

The algorithm identifies patterns of heterogeneity and selects a quantifying method, including methods for quantifying nonlinear and chaotic systems, such as ratios of genes expressions in adjacent cells, identifying patterns of variability in the metabolic activity in a tumor biopsy, for determining the type, dose and mode of administration of anti-tumor therapies. The number(s)/factor(s) which are generated by using the methods to quantify the pattern(s) of variability are used for design of new drugs, or are incorporated into drug treatment regimens, including alternating between different drugs for the same disease in the same patient.

Example 2: Determining and Quantifying Single Cell Variability Patterns Before and After Therapy A dataset of variability patterns at the cellular levels is generated using several single cell-based techniques. Assessments of single cell variabilities in gene expression are performed using single cell RNA sequencing; single cell proteomics; single cell metabolomics; single cell epitopes expression and cytokine secretion. Cell are harvested from patients before and after chronic disease therapy. The results are incorporated into a database. A method for quantifying the variability patterns is selected, based for example on methods for quantifying nonlinear or chaotic systems; methods for quantifying entropy; use of ratios between two consecutive measurements; mean of ratios of variabilities between two or more consecutive measurements; sample entropy algorithm; complexity index; multiscale entropy measurements; and any type of combinations of methods, which are used for signifying variability pattern(s). The resulting number(s)/factor(s), which are generated by using one or more of these methods are implemented into operating systems for improving their function and for reaching a pre-determined goal.

Example 3: Use of an App with a Pre-Determined Dosing Schedule for Improving the Response to Drugs Taking a constant dose of a drug on a regular basis, or continuously increasing their dose, increase serum drug levels which reaches a peak level, and then gradually decreases. The process repeats itself on a daily basis. It is a monotonic cyclic pattern which is associated with adaptation to the drug, and ends up with partial or complete loss of a response. A similar adaptation occurs for the drug-effect leading to resistance. A constant daily dose, or a continuous increase of a dose, are associated with drug-tolerance and resistance.

The closed loop system may improve the effectiveness of chronic drugs by altering the regular dosages and the intervals between dosages while keeping them within a range determined by the physician, and within the therapeutic window of the drug, as a method for overcoming drug habituation and improving efficacy. The treatment regimens are based on aperiodic routines of taking the medication at irregular intervals and at irregular strengths, without changing the total daily dosages, or on alternating between drugs which target the same disease. Irregular, pulsed, or multiple intervals-based administrations of chronic drug, and at continually changing dosage strengths can improve the overall effect, reducing drug resistance.

Each of the studies below includes subjects that partially lost the effect, or develop partial resistance to a chronically-administered drug, by introducing irregularity into the treatment regimens while keeping dosages within a pre-determined range.

i. Patients Who Lost the Effect of Anti-Epileptic Drugs

Epilepsy affects over 70 million people worldwide. Despite the recent introduction of new anti-seizure drugs (ASDs), about one-third of patients with epilepsy have seizures refractory to pharmacotherapy. Patients with drug-resistant epilepsy are enrolled in a study to determine the effect of introducing irregularity into their treatment regimens, while keeping them on the same drugs and within their physician's pre-determined range.

ii. Patients Who Lost the Effect of Anti-Depressant

A significant proportion of depressed patients eventually present with treatment-resistant/refractory major depression (TRD). Depression is considered resistant when at least two trials with antidepressants from different pharmacologic classes, which are adequate in terms of dose, duration, outcome, and compliance, failed to achieve remission. The current therapy for TRD involves the evaluation of comorbid medical and psychiatric conditions, augmentation, combination, and switching of anti-depressants. However, majority of TRD patients do not adequately respond. Patients treated with Zoloft and suffering from a partial loss of effect are enrolled in a study to determine the effect of introducing irregularity into the dose and times of administration while keeping the dosages within a predetermined regimen.

iii. Congestive Heart Failure with Diuretic Resistance

Heart failure (HF) is associated with significant mortality, morbidity, and healthcare expenditures. Much of the morbidity and reduced quality of life are related to symptoms of volume overload. Loop diuretics are a mainstay in the management of volume overload and edema. Diuretic resistance is defined as failure to achieve effective congestion relief despite appropriate or escalating diuretic doses. Such resistance is associated with a poor prognosis. Resistance to loop diuretics is associated with many factors, several of which are related to continuous daily administration of similar or higher dosages, leading to further reduction in response to therapy. In the study the effectiveness of an app which alters the regularity of the dosages and the intervals between the dosages while keeping them within a range determined by the physician, and within the regulatory approved therapeutic window, are used as a method for overcoming drug habituation and improving efficacy.

iv. Diabetes Type 2 with High Degree of Insulin Resistance

Insulin resistance in patients with diabetes mellitus (DM) is characterized by an impaired response to either endogenous or exogenous insulin. An increasing number of patients develop severe insulin resistance and require large doses of insulin. Patients who require >1 unit/kg/day are considered to have insulin resistance, and those requiring >2 units/kg/day have severe resistance. Alternatively, a total daily insulin dose of >200 units is commonly considered to be evidence of severe insulin resistance. The effectiveness of a basal-bolus insulin pump which alters the regularity of the dosages and the intervals between the dosages while keeping them within an overall daily range determined by the physician, as a method for alleviating the resistance and reducing the overall insulin requirement is assessed.

v. Patients with Chronic Pain on High Dosages of Pain Killers

Opiates are the primary treatment for pain management in cancer patients with moderate to severe pain, and are increasingly used for non-cancer chronic pain. Patients often develop tolerance to opioids over time with aggravated pain. Prolonged administration of opiates is associated with antinociceptive tolerance; wherein higher doses of the drug are required over time to elicit the same amount of analgesia. Sustained exposure to morphine can result in paradoxical pain in regions unaffected by the initial pain complaint, and result in dose escalation, i.e. 'analgesic tolerance'. The effectiveness of an app which alters the regularity of the dosages and the intervals between the dosages while keeping them within a range determined by the physician, and within the regulatory approved therapeutic window of the narcotics, in patients with partial tolerance to narcotics is determined. The level of pain and total dosages required is monitored as a method for assessing the reduced habituation and improved tolerance.

vi. Patients with Inflammatory Bowel Disease with Loss of Response to Anti TNF-Based Therapies Loss of response (LOR) to anti-TNF therapy is common among patients with inflammatory bowel disease patients and creates a management challenge to physicians. The incidence of LOR among adult IBD patients undergoing anti-TNF based therapy is 36%, and some studies suggested that up to 50% of patients with ulcerative colitis (UC) or Crohn's disease (CD) experience a LOR to infliximab after an initial response to the drug. In this example patients with Crohn's disease who experienced LOR, are enrolled in a study to determine the effect of introducing irregularity into the treatment regimens for overcoming the loss of effect. Clinical and laboratory endpoints are used for assessing the effect of the dosing regimen on the disease.

vii. Patients with Parkinson's Disease

Dosing patients with Parkinson's disease can be performed by introducing into the algorithm number(s)/factor(s) derived from analyzing their increased variability in gate combined with other variability patterns and other signatures such as from genetic patterns. These number(s)/factor(s) are based on quantifying and analyzing the data from a single or from multiple subjects. The response to the new algorithm can also be followed by reversing the change of variability towards a "healthier variability pattern".

Example 4: Implementing Variability Pattern(s) into Individualized-Treatment Algorithms of Chronic Diseases for Overcoming Drug Resistance In this study identifying patterns of variabilities in the response to chronic medications is used. A personalized drug regimen is delivered to a patient with chronic disease by an app. The app receives data on the subject variability pattern (s), and data on variability patterns from other patients with similar/non-similar diseases. These patterns relate both to inherent variability patterns such as heart rate variability, and glucose level variability, or cellular variability patterns, such as genetic variability. A method is used for quantifying these inherent variability patterns and for generating a personalized-variability number(s)/factor(s), for example by using the ratio between heart variability of two consecutive beats; use of methods to quantify non-linear and chaotic systems; use of sample entropy algorithm; use of a complexity index; use of multiscale entropy measurements; using ratio between variabilities of subsets of immune cells in subject's peripheral blood, and alike. The number(s)/factor(s) are incorporated into the treatment regimens with and without the use of a learning algorithm. Patients are followed for their clinical response and for the total amount drug required to achieve the target endpoints.

A clinically meaningful-endpoint is set for the algorithm. The algorithm selects one of more of several individualized-variability patterns based on patient's response. The algorithm incorporates data for other patients. It identifies the preferred variability pattern(s) and selects the preferred method to quantify them. Factors, generated by quantifying one or more of the inherent variability patterns with or without combining them with other patterns, are implemented into the treatment regimen which generates an individualized type of irregularity in the treatment, or any other regimens.

The response of the patient to the change induced by the algorithm, is assessed by the clinical parameters, as well as by measuring a change of the variability following introducing the therapy, Thus the pattern(s) of variability can be used as a biomarker for follow up of the effect of therapy on the disease.

A database of variabilities is generated in two cohorts of patients. Patients with congestive heart failure are followed for assessment of their heart rate variabilities in a 24 hours' measurement. Patterns of variabilities are defined and correlated with their clinical status. The pattern of heart rate variability of each patient is also compared with the subject's heart recordings prior to the deterioration of the disease.

Current management of type 2 diabetes focuses on lowering mean blood glucose values toward a normal range. However, these treatment regimens disregard the dynamics of glucose fluctuations. An analyte time series obtained from continuous glucose monitor (CGM) sensors in these patients showed that the fluctuations in CGM values sampled every 5 min are not "uncorrelated noise". A multiscale entropy analysis quantified the complexity of the temporal structure of the CGM time series sowing that the dynamics of glucose fluctuations from control subjects are more complex than those of subjects with type 2 DM over time scales ranging from about 5 min to 5 h. Patients are followed for patterns of glucose level variabilities. These patterns of variabilities are quantified. The number(s)/factor(s) are implemented into the treatment algorithms. Integrations these-number(s)/factor(s) with those from other levels such as genes and metabolome patterns, from the same patient and from other patients, is performed.

Example 5: Use of an App with a Closed Loop Learning of Intra and Inter Subject Variability Pattern(s) for Improving the Response to Drugs or to Medical Devices In patients with congestive heart failure, introducing number(s)/factor(s) generated based on the heart rate variability into a treatment regimen, such as the ratio between two consecutive heartbeat variabilities, may improve the response to diuretic therapy. If the patient already experienced loss of the heart rate variability, introducing the change in therapy can be followed by monitoring the effect of treatment on reversal of this loss. A use of previous electrocardiogram strips from the subject may enable to generate a "healthier-pattern of variability". Based on the patient's variability pattern the app determines a dynamic individualized irregularity pattern for a dosing regimen.

Example 6: A Personalized-Pacemaker

Based on individualized patterns of variability including heart rate variability when the patient was healthy, breathing variability, pulmonary artery pressure variability, or any other individualized patterns, including gene networks, are used for improving heart function and clinical status of a patient with congestive heart failure by implementing into the heart rhythm provided by the pacemaker a personalized variability pattern. The "individualized pacemaker", rather than providing a pre-determined regular constant rate, provides a heart rate variability within a specific range determined by the variability patterns learned from the subject, other patients with similar diseases, and from response to therapy. The variability introduced by the pacemaker can be dynamic and change over time according to input receives from the patient's variability pattern(s) or other inputs. If the patient already experienced loss of the heart rate variability, introducing a change in therapy is monitored by the partial reversal of the loss of change in one or more of the patterns of variability. These reversals are used as one of the measures for determining the output of the algorithm.

Examples 7: A Personalized Ventilator

Based on individualized patterns of breathing variability, or any other individualized data, improving the clinical effect of ventilators in the acute or chronic settings is performed. The ventilator provides a change in pressures, oxygenations, and rhythms, or any other parameter in the ventilator, to include, in addition to the constant parameters, patterns of variabilities learned from the subject, or from other healthy subjects, or from subjects with similar disorders, for improving oxygenation, and assist in weaning, by using an individualized-type of ventilating. The changes introduced into the operating system of the ventilator can be dynamic based on a continuous or a semi continuous input receives from the subject.

Example 8: A Personalized Dialysis Machine

Based on the individualized variability patterns and/or any other individualized data and/or data from other patients with acute or chronic kidney diseases, the dialysis regimen of a subject is continuously or semi continuously being altered, for achieving better performance as assessed by clinical and laboratory parameters. The software of the machine is altered in an individualized way which incorporates the variability patterns in kidney functions, or of any other type of personalized variability pattern, or any other type of a pattern, for shortening the dialysis and improving its effect. For example, the rate of the dialysis and percentages of the solutions used, or any other parameters, are continuously or semi continuously changed based on feedback received from the patient.

Example 9: A Personalized Drug-Pumps

These include any type of insulin pumps, chemotherapy pumps, pain killers-administration pump, intrathecal pumps, diuretic pumps, and alike, which work via a closed-loop integrating into their operating systems methods or algorithms which incorporate personalized-variability pattern(s).

Managing patients with severe insulin resistance is challenging because it is difficult to achieve good glycemic control using conventional treatment approaches. The algorithm identifies patterns of variability in glucose levels in each subject and implement them into a treatment schedule of the basal-bolus insulin pump which alters the regularity of the dosages and intervals between dosages, as a method for alleviating resistance and reducing overall insulin requirement. For pain-killer pumps, the goal is reducing the amount of painkillers administered to the patient by implementing inherent variability patterns into the treatment algorithm.

Example 10: A Personalized Nerve Stimulator

The nerve of muscle stimulator is used for reducing pain, or for improving muscle performance, works via a closed loop, which comprises personalized variability pattern(s) with or without additional data from the subject, other non-variable parameters, and data from other subjects. It improves the effect of the device for reducing acute or chronic pain and muscle performance.

Example 11: Cyber Security Dynamic Random Algorithm

Cryptography is a method of protecting information and communications through the use of codes. Computer-generated random type of coding is a common method used for cryptography. The goal is to improve the level of protection of cyber security algorithms by implementing into them individualized-patterns of variability. Any type of cyber security can be used in a dynamic individualized-way which is based on the subject's one or more inherent variability patterns and other patterns. By using a subject-tailored variability patterns for introducing randomness into these cryptography algorithms, an improved performance with higher degree of security is achieved. For example: implementing number(s)/factor(s) generated based on these patterns into an algorithm for determining a security code for the subject's bank account, car code, encryption of personal computers, and other personal belonging, are performed. The codes are altered continuously or semi continuously based on changes in the subject's variability-patterns. For example: when asked to type in a code for a bank account the subject puts in a number/factor that is generated online based on an online measurement of the subject's heart rate variability. It produces a dynamic type of personalized-type of cyber security, cryptography, and encryption, based on the introducing of an individualized type of variability into the system. It is better than fingerprint which is a constant and can be copied.

Example 12: Algorithm-Based Security Patrols

Any type of an irregular algorithm which is used for determining the function of security patrols can be improved by implementing into the algorithm personalized dynamic variability patterns of the guards as individuals or as a group.

Example 13: Home Devices and Devices Used for Preparing Goods for People: A Dynamic-Individualized Coffee Machine Home devices used by humans or for humans can be improved by implementing into them an individualized pattern whether it is an inherent variability pattern or other individualized parameters. An individualized-coffee machine receives data from the subject which comprises heart rate variability, mood scale, degree of happiness, degree of tiredness, and alike. Using a method to quantify these parameters, it prepares an individualized type of coffee. The algorithm implements the data from the subject and from other subjects and from database, in a way by which the machine knows whether the subject, better enjoys a certain type of coffee, or a certain way of preparing the coffee. Based on the subject's response, the device learns how to prepare the next cup for the subject and incorporates the data into its database. Any parameter which is used by a coffee machine, such as temperature, type of coffee beans used, time, and pressures used during the preparation, are altered based on the inherent variable and non-variable personalized parameters. As these parameters are continuously or semi continuously changing, the individualized coffee maker is a dynamic machine which can fits itself to the user's fluctuations.

A personalized smartphone is designed by implementing variability patterns, and other personal parameters into functions of the cell phone. These include the degree of lightening of the screen, as well as any complex functions of the phone. These parameters are altered continuously or semi-continuously, impacting the operating system of a device in a subject-tailored way.

Example 14: Improving Safety of Driving by Introducing Variabilities in an Individualized Way Visual attention to the driving environment is important for road safety. Eye glance behavior has been used as an indicator of distracted driving. Drivers with a higher scanning disorder level shift their main attention from surrounding areas towards phone area when engaging in visual-manual tasks. Monitoring heart rate or breathing variabilities while driving for keeping alertness of the driver and/or the passengers is suggested. Changes are made for improving the level of alertness based on the individualized parameters of variability, or on other type of parameters. These changes include alterations in volume of music, smells, temperature, and movement of chairs inside the car, and alike, while the driver's parameters are being continuously/semi continuously monitored for alertness.

An attention-based brain-computer interface (BCI) paradigm uses visual or auditory, or smell, or temperature parameters. BCI has an advantages of high information transfer rate, high tolerance to artifacts, and robust performance across users. It is associated with mental load and fatigue occurring in the concentration on visual, motion, auditory or any other type of stimuli. Irregularity is a random perturbation with the power of randomness. It can be exploited by the human brain to enhance higher-level brain functions. Introducing an irregularity in auditory noises, temperatures, movements of the chair, can alleviate the mental load and fatigue during driving. In this example adding individual parameters based on variability-patterns as well as other personalized signatures, are incorporated into these irregularity generating-algorithms, for individualizing them in a dynamic way.

Example 15: Improving the Function and Pleasure of Riding an Autonomous Car

Any type of car moving patterns used in an individualized-way based on subject variability or other personal patterns. Introducing passenger-based car algorithms for autonomous cars which fit the passenger's personalized parameters, for improving the pleasure of a ride. Different sensors are used for follow up of variability parameters. Once the subject gets into the car, the car senses the type of driving that fits the subject's parameters, or subject's mood as reflected by these measures. These may be changed during the drive such that if the mood of one of the passengers is altered during the trip, leading the car to respond accordingly. The car changes its speed, the temperature inside the car, level of music, or lightening inside the car, in response to changes in patterns of variability of the passengers.

Example 16: Alleviation of Unpleasant Symptoms while Driving an Autonomous Car and Modeling an Autonomous Car Interaction with Other Cars, Pedestrians, and Cyclists Subjects performing non-driving tasks inside an autonomous car can develop motion sickness. Peripheral information delivered by different sensors, including analyzed variability patterns of the subject are incorporated into the algorithm for generating a type of a drive that which alleviate these symptoms.

A model for the car driver and bicycle cyclist interactions when they are approaching a conflicting zone which is based on comprising variability patterns, can benefit from introducing irregularity parameters into the response of the car. The model can apply randomness of the location of the cars' decision points in a passenger-tailored way.

Example 17: Improved Learning and Training by Implementing Inherent Variability Patterns Improving exercise/training/teaching/learning/playing/ education regimens/nutritional regimens by implementing into the learning or training regimens at least one inherent variability patterns. For example, the heart rate variability and breathing variability patterns may be measured continuously or semi continuously, while a subject is running on an elliptical and the speed and degree of difficulty of the machine are altered accordingly with a goal of shortening the time of exercise and improving the results of the training.

Example 18: An Individualized-Variability Based Search Engines

Search engines are designed to provide lists of findings which are tailored to the user based on pre-determined algorithms. Introducing inherent variability patterns into these engines may provide an additional method for individualizing the search results. The list of results is individualized, based on a personalized-irregularity which fits one or more of the inherent variability parameters of the subject.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

I claim:

1. A computer implemented method for improving function of one or more biological system of a subject in an individualized way, and/or for overcoming partial or complete loss of effect, non-responsiveness, and/or partial or complete resistance of one or more biological systems to a treatment regimen, by identifying, quantifying, and/or implementing at least one inherent variability pattern, which is based on patterns learned from the subject and/or from other subjects, the method comprising:

identifying intra subject and/or inter subjects variability patterns or parameters, one or more non-variable individualized patterns or parameters and/or nonlinear networks and chaotic parameters;

identifying internal or external triggers, including those from other subjects, the environment, and non-subject related triggers;

quantifying the one or more variability patterns or parameters, and one or more non-variable individualized patterns or parameters nonlinear networks and chaotic parameters;

combining the quantified intra subject and/or inter subjects variability patterns, and internal or external triggers, nonlinear networks and chaotic parameters, and/or non-variable individualized patterns with the subject's own patterns of function in one or more biological systems for providing one or more combined patterns or parameters;

incorporating the one or more of the combined patterns or parameters into treatment regimens by applying a closed-loop machine learning algorithm comprising deep learning capabilities in which the learning on some features is guided or supervised learning, while learning on other features is unguided or unsupervised learning, to the one or more of the combined patterns or parameters;

determining subject-specific output parameters relating to at least one target system function by applying irregularity generating-algorithms, for determining irregularity in dosage and/or in time interval ranges for one or more drugs administration to the subject;

utilizing the subject-specific output parameters to improve the at least one target system function by using the deep machine learning algorithm by applying a subject-tailored continuously or semi continuously inherent variability pattern, thereby facilitating continual improvement of the target system; and administering to the subject the one or more drugs according to the irregularity in dosage and/or time interval ranges.

2. The method of claim 1, wherein the at least one inherent variability pattern comprises: variability patterns at the level of DNA, RNA, proteins, cellular functions, cell signaling products, cell apparatuses, body organs, biological pathway (s), proteome, metabolome, lipidome, microbiome, organs, whole body and/or any type of network-based variability.

3. The method of claim 1, further utilized for improving function and/or performance thereof and for individualizing treatment regimens and/or devices and for improving their efficacy for reaching goals determined by the subject, the system, or by other subjects, optionally additionally using updated at least one of the subject-specific output parameters.

4. The method of claim 1, wherein the machine learning algorithm takes into account personal data including any type of individualized-inherent variability patterns and wherein at least one of the physiological and/or pathological parameters is obtained from a sensor.

5. The method of claim 1, further comprising providing to the subject, to a device, or to the target system a recommended regimen or changes thereto.

6. The method of claim 5, wherein the providing of the recommended regimen or changes thereto is in real time.

7. The method of claim 1 wherein the deep learning capabilities are configured to operate on a set of features by receiving values thereof, and wherein a number of layers and/or levels of the deep machine learning depends on the number of features.

8. The method of claim 1 used for improving tissue, organ and/or body system function in healthy or sick subjects, wherein the tissue, organ and/or body system comprises:

muscle, heart, lung, skin, brain, liver, pancreas, bladder, uterus, kidney, cardio vascular system, lymphatic system, immune system, hormonal system, genital system, nerve system, skeletal system or any combination thereof.

9. The method of claim 1 used for improving training, learning and/or teaching capabilities.

10. The method of claim 1 used for treatment of obesity, infectious, metabolic, endocrinology, malignant, immune-mediated, inflammatory condition, inborn error of metabolism, pain, microbiome-related disorders, neurological disease, fibrosis in an organ, desynchronosis, circadian dysrhythmia or any combination thereof.

11. The method of claim 1 used for improving drug treatment regimens, redesigning of structure of drugs, for overcoming drug resistance, for improving a clinical effect of a medical device.

12. The method of claim 11, wherein the medical device comprises a pacemaker, ventilator, dialysis machine, pump for delivering drugs.

13. The method of claim 1, wherein the irregularity generating algorithms comprise random or pseudo random number generating algorithms.

14. A computerized system configured to implement the method of claim 1.

15. A computer readable non-transitory storage medium comprising instructions which cause one or more processors to perform the method of claim 1.

* * * * *